(12) United States Patent
Kellenberger et al.

(10) Patent No.: US 7,338,625 B2
(45) Date of Patent: Mar. 4, 2008

(54) METHODS OF RESTORING ELASTICITY AFTER STIFFENING TREATMENTS

(75) Inventors: Stanley R. Kellenberger, Appleton, WI (US); Vincent B. Newbill, Cumming, GA (US); Anthony John Wisneski, Kimberly, WI (US); Wendy L. VanDyke, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 656 days.

(21) Appl. No.: 10/246,775

(22) Filed: Sep. 18, 2002

(65) Prior Publication Data
US 2004/0051199 A1 Mar. 18, 2004

(51) Int. Cl.
*B29C 67/00* (2006.01)

(52) U.S. Cl. ............... 264/136; 264/137; 264/284; 264/288.4

(58) Field of Classification Search ............... 156/229, 156/161, 269, 164, 163, 264, 358; 264/136, 264/137, 171.13, 284, 288.4, 290.2
See application file for complete search history.

(56) References Cited

U.S. PATENT DOCUMENTS

| | | | |
|---|---|---|---|
| 20,383 A | 5/1858 | Whitmarsh |
| 1,575,003 A | 3/1926 | Recher |
| 1,741,530 A | 12/1929 | Mayer |
| 1,823,053 A | 9/1931 | Lawton |
| 2,004,110 A | 6/1935 | Head |
| 2,093,904 A | 9/1937 | Bierer |
| 2,188,332 A | 1/1940 | Carothers |
| 2,224,992 A | 12/1940 | Sutherland |
| 2,353,525 A | 7/1944 | Teague |
| 3,047,444 A | 7/1962 | Harwood |
| 3,255,030 A | 6/1966 | Storti |
| 3,325,338 A | 6/1967 | Geen |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,976,075 A | 8/1976 | Chinai et al. |
| 4,100,324 A | 7/1978 | Anderson et al. |
| 4,318,408 A | 3/1982 | Korpman |
| 4,340,563 A | 7/1982 | Appel et al. |
| 4,381,320 A | 4/1983 | Nguyen |
| 4,443,511 A | 4/1984 | Worden et al. |
| 4,500,315 A | 2/1985 | Pieniak et al. |
| 4,525,407 A | 6/1985 | Ness |
| 4,692,368 A | 9/1987 | Taylor et al. |
| 4,721,647 A | 1/1988 | Nakanishi et al. |

(Continued)

FOREIGN PATENT DOCUMENTS

EP 0 040 087 A2 11/1981

(Continued)

Primary Examiner—N. Edwards
(74) Attorney, Agent, or Firm—Pauley Peterson & Erickson

(57) ABSTRACT

Methods for restoring elasticity to a stiffened elastic material include prestretching, compressing and/or notching the stiffened elastic material. These methods can be used alone, or in combination for a compounding effect.

41 Claims, 8 Drawing Sheets

U.S. PATENT DOCUMENTS

| | | |
|---|---|---|
| 4,778,460 A | 10/1988 | Braun et al. |
| 4,855,179 A | 8/1989 | Bourland et al. |
| 4,891,258 A | 1/1990 | Fahrenkrug |
| 5,021,050 A | 6/1991 | Iskra |
| 5,071,681 A | 12/1991 | Manning et al. |
| 5,098,775 A | 3/1992 | Harada et al. |
| 5,100,397 A | 3/1992 | Poccia et al. |
| 5,126,382 A | 6/1992 | Hollenberg |
| 5,139,841 A | 8/1992 | Makoui et al. |
| 5,171,237 A | 12/1992 | Poccia et al. |
| 5,226,992 A * | 7/1993 | Morman .................... 156/62.4 |
| 5,246,429 A | 9/1993 | Poccia et al. |
| 5,422,172 A | 6/1995 | Wu |
| 5,458,592 A | 10/1995 | Abuto et al. |
| 5,466,731 A | 11/1995 | Akers et al. |
| 5,480,693 A | 1/1996 | Patterson et al. |
| 5,486,166 A | 1/1996 | Bishop et al. |
| 5,490,846 A | 2/1996 | Ellis et al. |
| 5,520,673 A | 5/1996 | Yarbrough et al. |
| 5,649,916 A | 7/1997 | DiPalma et al. |
| 5,693,707 A | 12/1997 | Cheng et al. |
| 5,882,769 A | 3/1999 | McCormack et al. |
| 5,962,068 A | 10/1999 | Tsuchiya et al. |
| 6,027,804 A | 2/2000 | Chou et al. |
| 6,060,409 A | 5/2000 | Cochran |
| 6,103,358 A | 8/2000 | Brüggemann et al. ... 428/317.9 |
| 6,103,809 A | 8/2000 | Ahmed et al. |
| 6,129,801 A * | 10/2000 | Benson et al. .............. 156/229 |
| 6,162,541 A | 12/2000 | Chou et al. |
| 6,203,845 B1 | 3/2001 | Qin et al. |
| 6,207,237 B1 | 3/2001 | Haffner |
| 6,217,692 B1 * | 4/2001 | Kling ......................... 156/229 |
| 6,248,851 B1 | 6/2001 | Maugans et al. |
| 6,265,045 B1 | 7/2001 | Mushaben |
| 6,362,389 B1 * | 3/2002 | McDowall et al. ......... 604/367 |
| 6,369,293 B1 | 4/2002 | Reeves et al. |
| 6,417,425 B1 | 7/2002 | Whitmore et al. |
| 2004/0054341 A1 | 3/2004 | Kellenberger et al. |
| 2004/0054342 A1 | 3/2004 | Newbill et al. |

FOREIGN PATENT DOCUMENTS

| | | |
|---|---|---|
| EP | 223 908 | 6/1987 |
| EP | 293 762 | 12/1988 |
| EP | 0 333 515 A2 | 9/1989 |
| EP | 0 188 091 B1 | 3/1991 |
| EP | 0 708 119 A1 | 4/1996 |
| EP | 251 314 | 1/1998 |
| EP | 262 405 | 4/1998 |
| EP | 0 651 631 B1 | 6/1999 |
| EP | 0 794 751 B1 | 6/1999 |
| EP | 0 947 549 A1 | 10/1999 |
| EP | 947 549 | 10/1999 |
| JP | 57-110123 | 7/1982 |
| JP | 61-055202 | 3/1986 |
| JP | 62-027413 | 2/1987 |
| JP | 62-053479 | 3/1987 |
| JP | 62-062829 | 3/1987 |
| JP | 62-097978 | 5/1987 |
| JP | 62-097979 | 5/1987 |
| JP | 62-210054 | 9/1987 |
| JP | 62-243606 | 10/1987 |
| JP | 11-21308 | 11/1987 |
| JP | 01-203084 | 8/1989 |
| WO | WO 94/02094 | 2/1994 |
| WO | WO 97/27884 | 8/1997 |
| WO | WO 97/43480 | 11/1997 |
| WO | WO 98/37846 | 9/1998 |
| WO | WO 99/10591 | 3/1999 |
| WO | 00/50096 | 8/2000 |
| WO | WO 00/44556 | 8/2000 |
| WO | WO 00/50096 | 8/2000 |
| WO | WO 00/58546 | 10/2000 |
| WO | 01/56625 | 8/2001 |
| WO | 01/87589 | 11/2001 |
| WO | WO 01/87589 A2 | 11/2001 |

* cited by examiner

METHODS OF RESTORING ELASTICITY AFTER STIFFENING TREATMENTS

BACKGROUND OF THE INVENTION

This invention is directed to methods of restoring elasticity to elastic material after the elastic material has been stiffened by attaching another material to it.

In order for most nonwoven materials to be stretchable and elastomeric, the individual fibers must be able to move away from one another or even across one another when the material is stretched. Anything that hinders this free movement will cause an increase in the elastic modulus of the material because more force or a higher load is required to stretch the material. Furthermore, if the elastic material is stretched beyond the yield point of the bonds that may exist between the fibers of the elastic material, the material will not contract to the original length. That is, the elastic modulus is not only higher, but there will also be significant non-recoverable stretch (i.e., hysteresis) if the material is stressed beyond its yield point.

For example, when liquid material (e.g., superabsorbent polymer solutions or prepolymer) is applied and/or attached by saturation, coating, printing or spraying onto an elastomeric web and is then polymerized, crosslinked and/or cured, the now solid material bonds groups of fibers together. Bonds between the fibers result in an increase in the elastic modulus of the elastic material because the fibers will not be free to move relative to each other. The bonds also cause the surface of the material to become rough and stiff. Both of these results are undesirable for personal care garments. It is important that material be soft so that personal care garments are comfortable and have an elastic modulus that is low enough to provide the desired ease of stretching for personal care garments.

FIG. 1 shows load vs. elongation extension and retraction curves for an elastomeric high-loft bonded carded web which has been treated with a superabsorbent polymer as well as the same elastomeric high-loft bonded carded web which has not been treated (i.e., untreated) with a superabsorbent polymer. The superabsorbent polymer in this instance was produced using the application and polymerization teachings in U.S. Pat. No. 4,500,315 issued 19 Feb. 1985 to Pieniak et al., and U.S. Pat. No. 6,417,425 issued 09 Jul. 2002 (previously published as PCT Publication No. WO 01/56625) to Whitmore et al., both of which are incorporated herein by reference.

As shown in FIG. 1, the extension curve (i.e., the diagonal line) for the treated (superabsorbent prepolymer material applied, polymerized, crosslinked and dried on) elastomeric high-loft bonded carded web material shown with the upward pointing arrow represents the load (in grams) required to elongate a two (2) inch wide strip of the treated material to the corresponding percentage elongation on the x-axis. The retraction curve (with the downward pointing arrow) represents the load measurements when the treated material was allowed to retract as the deforming load was removed. The decrease in load at all levels of elongation as the material was allowed to retract indicates that the material was weakened from the bonds between the fibers and superabsorbent breaking due to the application of the deforming load.

The sample treated with the superabsorbent polymer exhibited an increase in elastic modulus (in grams). The load required to stretch the material 80% increased from about 100 g/2 inch width of material (for the untreated material) to about 2300 g/2 inch width of material (for the treated material). In addition, when allowed to retract by removing the deforming load significant hysteresis was shown with the treated material. The area between the extension and retraction curves for the treated material is the hysteresis loss.

However, as also shown in FIG. 1, the extension and retraction curves for the untreated elastomeric high-loft bonded carded web with accompanying nearly horizontal pointing arrows represent the load (in grams) required to elongate the untreated material to the corresponding percentage on the x-axis and the load measurements when the material was allowed to retract as the deforming load was removed. As shown, these two lines overlay each other, illustrating that the untreated material maintained its strength and was able to recover to its original unstretched length without any noticeable hysteresis loss.

FIG. 1 illustrates the huge effect on elastic properties that an attached material can have on an elastic material. It is apparent from this data that the elastomeric high-loft bonded carded web will perform significantly differently after the superabsorbent polymer is applied and/or attached. Furthermore, this data illustrates the importance of, and need for, a method of restoring the stiffened elastic material back to its original elastic properties.

There is a need or desire for methods of restoring elasticity to elastic material after the elastic material has been stiffened by applying and/or attaching another material to it.

SUMMARY OF THE INVENTION

In response to the discussed difficulties and problems, new methods have been discovered for restoring elasticity to elastic material after the elastic material has been stiffened by applying and/or attaching material to it. It has been discovered that stretching, compressing, and/or notching a stiffened elastic material are effective methods of restoring/recapturing the low modulus elasticity of the elastic material. These methods can be used alone or in combination for a compounding effect.

The present invention is directed to methods of restoring elasticity to elastic material after the elastic material has been stiffened by applying and/or attaching another material to it. Elastomeric webs that have attached materials can be returned to a state of near their original elastic state by using stretching, compressing and/or notching, or a combination of these methods. The finished elastic material with its elasticity restored is particularly suitable for use in personal care absorbent applications, medical garment applications, athletic garment applications and workwear garment applications.

One method of the present invention includes prestretching a stiffened elastic material. In this embodiment, the stiffened elastic material must be prestretched beyond which the finished material will be stretched in use, that is, beyond the "usable stretch amount" of the finished elastic material. Prestretching the stiffened elastic material will soften it and reduce its elastic modulus. When the stiffened elastic material is stretched beyond its yield point or elastic limit, the fibers that are bonded together as a result of the attached material are pulled apart resulting in a lowering of the elastic modulus. The prestretching removes the hysteresis before the finished elastic material is in actual use resulting in elastic stretch with no or very little hysteresis loss when being stretched in later actual use. Carrying out the prestretching operation with the attached material at low moisture content (less than about 10%, or less than about 5% or less than about 2%) will result in improved stretch properties at any given prestretch level or the same properties when prestretched to a lesser extent.

Another method of the present invention includes compressing the stiffened elastic material. When an elastic nonwoven material is compressed, the fibers are forced to move closer together. If there is an attached material on the elastic nonwoven, the attached material is flattened also. This action causes breaking of some of the bonds which formed between the fibers as a result of the attached material and a reduction in the elastic modulus of the elastic material. It has also been found that carrying out this compression step at very low moisture contents (less than about 10%, or less than about 5% or less than about 2%) is more effective probably due to the higher stiffness of the attached material at low moisture contents and therefore more susceptible to rupture of the application and/or attachment mechanism.

Another method of the present invention includes notching the stiffened material in order to reduce its elastic modulus. If transverse slits or notches are cut in a piece of elastic material, the notches effectively reduce the elastic modulus because many of the elastic filaments are cut. Also, the notches can open like windows and the elastic material can elongate as the opposing sides of the windows collapse toward one another. Notching does not break the bonds between the fibers caused by the attached material.

This invention makes it possible, for example, to in-situ polymerize superabsorbent polymer onto an elastomeric nonwoven and then soften it so as to make it suitable for personal care garments, medical garments, athletic garments and/or workwear garments.

With the foregoing in mind, it is a feature and advantage of the invention to provide methods of restoring elasticity to stiffened elastic material.

DEFINITIONS

Figure 1:
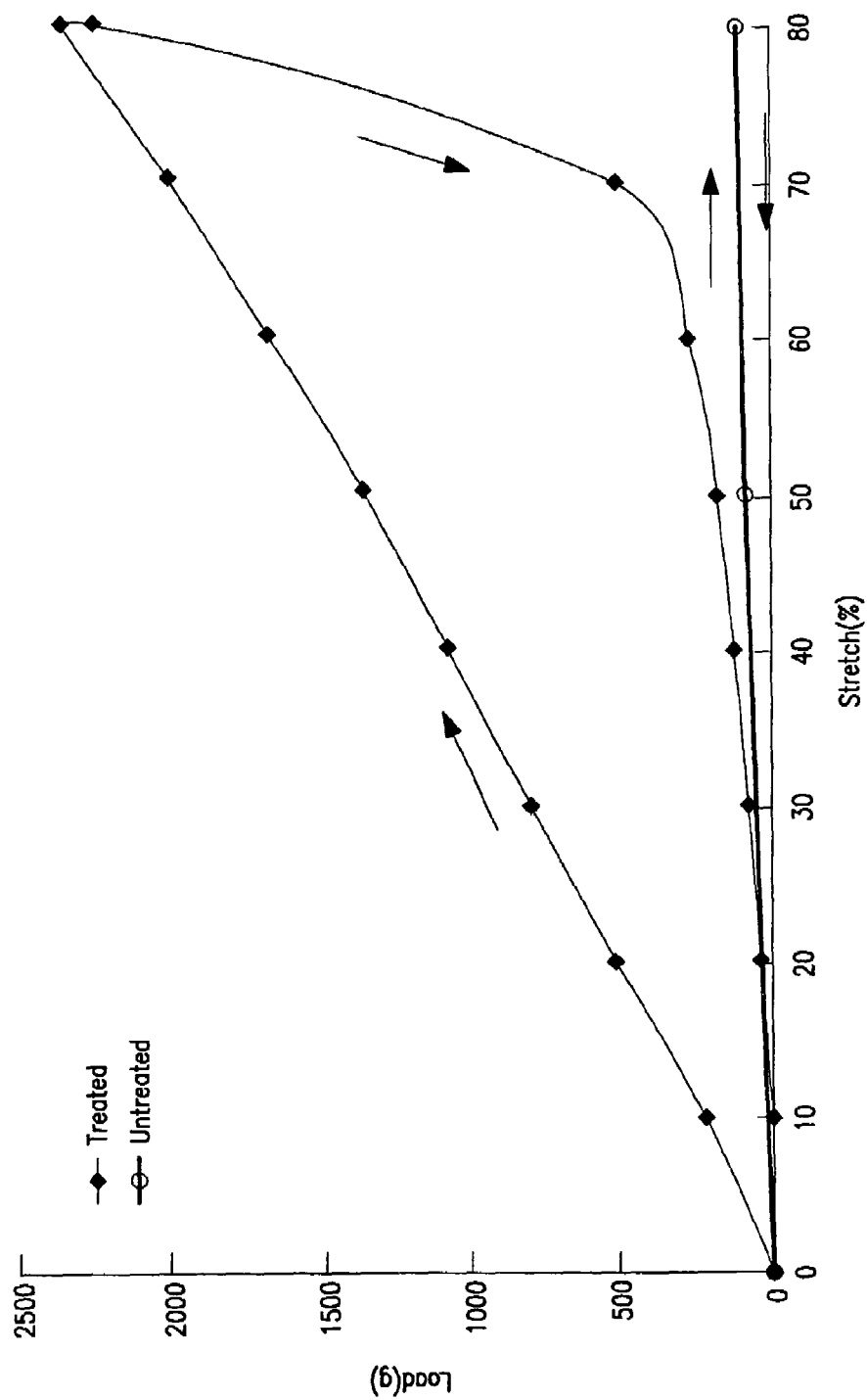
FIG. 1 illustrates load vs. elongation extension and retraction curves for an elastomeric high-loft bonded carded web, which has been treated with superabsorbent polymer (treated) as well as the same material which has not been treated (untreated) with superabsorbent polymer.

Within the context of this specification, each term or phrase below will include the following meaning or meanings. "Absorbent article" includes personal care garments, medical garments, athletic and workwear garments, and the like. The term "disposable garment" includes garments which are typically disposed of after 1-5 uses. The term "personal care garment" includes diapers, training pants, swim wear, absorbent underpants, adult incontinence products, feminine hygiene products, nursing pads, underarm pads, wipes, breathable-when-dry outer absorbent product covers, and the like. The term "medical garment" includes medical (i.e., protective and/or surgical) gowns, caps, gloves, drapes, face masks, bandages and the like. The term "athletic garments" includes athletic socks, pants, supporters, bras, shirts, sweat bands, helmet liners, and the like. The term "workwear garments" includes laboratory coats, coveralls, hard-hat liners, and the like. "Attached" refers to the joining, adhering, connecting, bonding, or the like, of at least two elements. Two elements will be considered to be attached together when they are attached directly to one another or indirectly to one another, such as when each is directly attached to intermediate elements. "Attached material" refers to a material, such as a superabsorbent polymer, which has been applied and/or attached to an elastic material.

"Bonded carded web" refers to webs made from staple length fibers that are carded into a web and then bonded by some technique such as thermal or adhesive bonding.

"Elastomeric" is the property of a material that refers to its ability to extend when under a load and recover a significant portion of the load-induced extension after the load is removed. "Elastomeric" and "elastic" are used interchangeably to refer to a material or composite that is generally capable of recovering its shape after deformation when the deforming force or load is removed. Specifically, as used herein, elastic or elastomeric is meant to be that property of any material which, upon application of an elongating force or load, permits the material to be stretchable to a stretched elongated length which is at least about 25 percent greater than its relaxed unstretched length, and that will cause the material to recover at least 40 percent of its elongation upon release of the stretching force or load. A hypothetical example which would satisfy this definition of an elastomeric material would be a ten (10) centimeter sample of a material which is elongatable to at least 12.5 centimeters and which, upon being elongated to 12.5 centimeters and released, will recover to a length of less than 11.5 centimeters. Many elastic materials may be stretched by much more than 25 percent of their relaxed length, and many of these will recover to substantially their original relaxed length upon release of the stretching force or load.

"Elastomeric high-loft bonded carded webs" are low-density webs that contain a means of rendering them elastomeric. An example of suitable materials of this type includes two layers of through-air-bonded 17 gram per square meter (gsm) polyester staple fiber with polyethylenesheath/polypropylene-core binder fiber carded web laminated to both sides of stretched, extruded and cooled KRATON® 6631 elastomeric polymer, available from Kraton Polymers, Belpre, Ohio, filaments with 1.5 gsm Findley 2096 adhesive, available from Ato-Findley, Inc., Wauwatosa, Wis., hot melt sprayed on each layer of web.

"Elastic modulus" refers to the amount of force, or load, needed to elongate an elastic material to a given length or distance which is less than the yield point of the elastic material (i.e. point at which permanent deformation begins). The lower the force or load required, the lower the elastic modulus. Conversely, the higher the force or load required, the higher the elastic modulus.

"Encase" refers to the act of surrounding, coating, or otherwise covering an object. It does not necessarily mean totally encase. It can mean partially encase.

"Film" refers to, for example, a thermoplastic film made using a film extrusion process, such as a cast film or blown film extrusion process. The term includes apertured films, slit films, and other porous films which constitute liquid transfer films, as well as films which do not transfer liquid.

"Foam" refers to two-phase gas-solid systems that have a supporting solid lattice of cell walls that are continuous throughout the structure. The gas, typically air, phase in a foam is usually distributed in void pockets often called cells.

"High-loft bonded carded webs" are low-density bonded carded webs often used for surge/acquisition functions in personal care garments.

"Hysteresis" refers to the ratio of the difference between the amount of energy put into a material when it is displaced, and the amount of energy recovered when the material is returned, usually measured as a percent loss of the energy put into the material.

"Layer" when used in the singular can have the dual meaning of a single element or a plurality of elements.

"Liquid-impermeable," when used to describe a layer or laminate means that liquid such as urine will not pass through the layer or laminate under ordinary use conditions in a direction generally perpendicular to the plane of the layer or laminate at the point of liquid contact.

"Liquid-permeable," refers to a layer or laminate that is not liquid impermeable.

The term "machine direction" refers to the length of a fabric in the direction in which it is produced, as opposed to "cross-machine direction" which refers to the width of a fabric in a direction generally perpendicular to the machine direction.

"Medicinal treatment" refers to any composition that alleviates pain, discomfort, or irritation, or has any other healing properties.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Meltspun fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Meltspun fibers are quenched and generally not tacky when they are deposited onto a collecting surface. Meltspun fibers are generally continuous and often have average deniers larger than about 0.3, more particularly, between about 0.6 and 10. "Spunbond" is often used synonymously with Meltspun especially when referring to a bonded web of Meltspun fibers.

"Nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, meltspinning processes, air laying processes, and bonded carded web processes. The term "Nonwoven" in the most general sense refers to any structure which is not woven and thus also includes structures like foams.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Prestretching" refers to stretching a material prior to the material's actual use or inclusion in articles.

"Stiffened elastic material" refers to an originally elastic material to which an attached material has been applied and/or attached, and as a result demonstrates an increase in its elastic modulus and demonstrates hysteresis loss.

"Stretchable" means that a material can be stretched, without breaking, by at least 25% (to 125% of its initial (unstretched) length) in at least one direction, suitably by at least 50% (to 150% of its initial length), desirably by at least 100% (to at least 200% of its initial length).

"Superabsorbent," "superabsorbent polymer," or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as polyphosphazenes, or organic compounds such as crosslinked polymers. Also included are materials which do not swell but have high enough internal capacities such as aerogels which are capable of absorbing at least about 15 and more desirably at least about 30 times their weight in an aqueous solution containing 0.9 weight percent sodium chloride.

"Superabsorbent retention" refers to the amount of superabsorbent that remains applied and/or attached to a web during or after use.

"Surge material" refers to a layer of material designed to rapidly accept fluid exudates and distribute the fluid exudates to a retention structure. Examples of suitable surge materials are described in U.S. Pat. No. 5,486,166 to Bishop and U.S. Pat. No. 5,490,846 to Ellis, both of which are herein incorporated by reference.

"Thermoplastic" describes a material that softens when exposed to heat and which substantially returns to a non-softened condition when cooled to room temperature.

"Thermoset" describes a material that is capable of becoming permanently cross-linked.

"Vertical filament laminate" refers to material made using a Vertical Filament Lamination (VFL) process, which is described in PCT Publication WO 01/87589, published Nov. 22, 2001, and entitled ELASTIC STRANDED LAMINATE WITH ADHESIVE BONDS AND METHOD OF MANUFACTURE by H. M. Welch et al., incorporated herein by reference. Briefly this refers to vertically extruding multiple filaments onto a quench roll, elongating the filaments, laminating the filaments to a contractible (e.g. bonded carded) web and then letting it contract thus creating, for example, an elastomeric high-loft bonded carded web.

"Yield point" refers to the force or load applied to stretch a material or the strain or distance the material is stretched beyond which the material will permanently deform.

These terms may be defined with additional language in the remaining portions of the specification.

DESCRIPTION OF PREFERRED EMBODIMENTS

The present invention is directed to methods of restoring elasticity to an elastic material after the elastic material has been stiffened by applying and/or attaching material (an "attached material") to it. For purposes of the present invention, after the attached material is applied and/or attached to the elastic material, the resulting material is referred to herein as a "stiffened elastic material." A "stiffened elastic material" includes an elastomeric material and an attached material, such as a superabsorbent polymer, applied and/or attached to the elastomeric material wherein the attached material causes stiffening of the elastomeric material.

One example of a stiffened elastic material is an absorbent, elastomeric material which includes an elastomeric substrate and a superabsorbent polymer applied and/or attached to the substrate without the use of bonding agents such as adhesives.

The elastomeric substrate, for example, can be an elastomeric high-loft bonded carded web, or can include an elastic component, such as an elastic film, an elastic foam, and/or a number of elastic strands, and may be laminated to at least one nonwoven web facing. Facing materials may be nonwoven webs formed using conventional processes, including bonded carded webs, or the meltspun and meltblowing processes described in the DEFINITIONS. For example, the facing sheets may each include a bonded carded web having a basis weight of about 3-150 gsm, suitably 6-75 gsm or about 10-25 gsm. The facing sheets in a single substrate may include the same or similar materials or different materials on each side of the elastomeric component. Suitably, the elastomeric substrate includes low density, open web facings, having a volume fraction (VF) of less than about 0.05, or less than about 0.04, or less than about 0.02. The VF of the open web facings is the volume of material per unit volume, and can be determined using the stereology methods taught in *Practical Stereology* by John C. Russ, published by Plenum Press, NY, N.Y. (1986). The determination of the VF of the open web facings using the stereology methods taught by Russ should be done in a manner that is representative of the VF of the facing material without the superabsorbent present. The open web facings suitably have a mean pore size greater than about 200 microns, or greater than about 400 microns, as determined using microscopic image analysis of the surface pores.

Any suitable form of bonding can be used to create the elastomeric substrate, including thermal, adhesive, or ultrasonic bonding, for example. In addition the elastomeric substrate can consist totally of an elastomeric foam made with suitable elasticity, cell size and VF. The elastomeric substrate can be stretched at least about 25%, or at least about 50%, or at least about 75% and can suitably retract at least about 40% of the stretched amount. Ideally the elastomeric substrate can be stretched these amounts in more than one direction but must elastically stretch in at least one direction most preferably in the Machine Direction (MD). The elastomeric substrate may be either liquid-permeable or liquid-impermeable, depending on the permeability of the elastic component regardless of whether the elastomeric substrate is in a stretched or unstretched state.

Materials suitable for use in preparing the elastic component, in the form of strands, film, and/or foam, include diblock, triblock, tetrablock, or other multi-block elastomeric copolymers such as olefinic copolymers, including styrene-isoprene-styrene, styrene-butadiene-styrene, styrene-ethylene/butylene-styrene, or styreneethylene/propylene-styrene, which may be obtained from Kraton Polymers, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cubic centimeter, available from Dow Chemical Co. under the trade name AFFINITY®.

A number of block copolymers can also be used to prepare the elastic component of the absorbent, elastomeric material. Such block copolymers generally include an elastomeric midblock portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastic component can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once crosslinked cannot be thermally processed, but can be obtained on a spool or other form and can be stretched and applied as strands in the same manner as thermoplastic polymers. As another alternative, the elastic component can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/ propylene polymers, ethylene/butylenes polymers, polybutadiene, and the like, or mixtures thereof.

Suitable block copolymers useful include at least two substantially polystyrene endblock portions and at least one substantially ethylene/butylenes mid-block portion. A commercially available example of such a linear block copolymer is available from Kraton Polymers under the trade designation KRATON® G1657 elastomeric resin. Another suitable elastomer is KRATON® G2760.

One example of making an elastomeric substrate includes the Vertical Filament Lamination of extruding one of the KRATON® thermoplastic elastomeric polymers, mentioned above, from a multi-hole die onto a chilled roll. The resulting elastic strands are then stretched by a series of rollers running at increasing speed before being laminated between lightweight high-loft bonded carded web facing materials that have been sprayed with hot melt adhesive just before entering the laminating nip. After the three parts are laminated together, the substrate is relaxed resulting in an elastomeric structure.

The elastic component may also contain blends of elastic and inelastic polymers, or of two or more elastic polymers, provided that the blend exhibits elastic properties.

Figure 2:
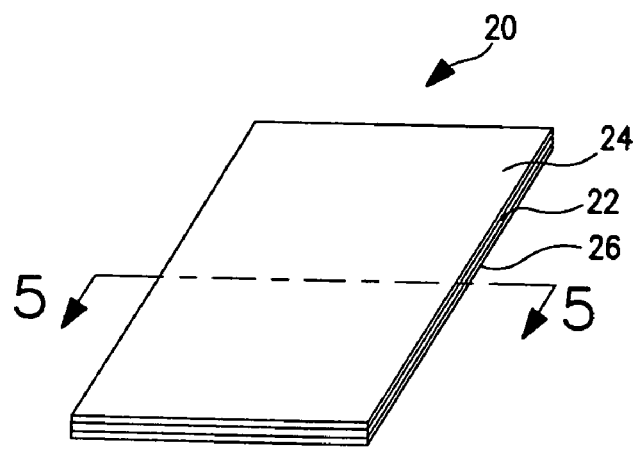
FIG. 2 is a perspective view of one embodiment of an elastomeric substrate used to make an absorbent, elastomeric material.
Figure 3:
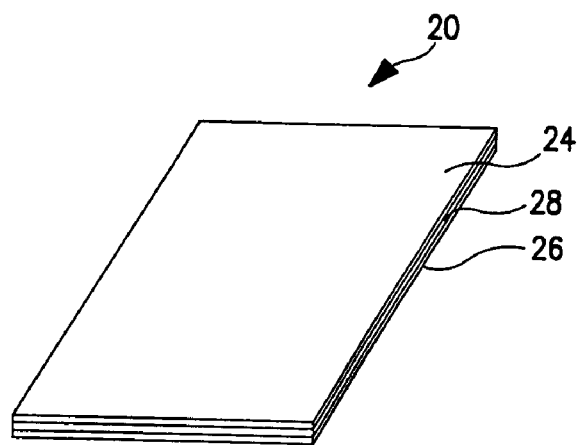
FIG. 3 is a perspective view of another embodiment of an elastomeric substrate used to make an absorbent, elastomeric material.
Figure 4:
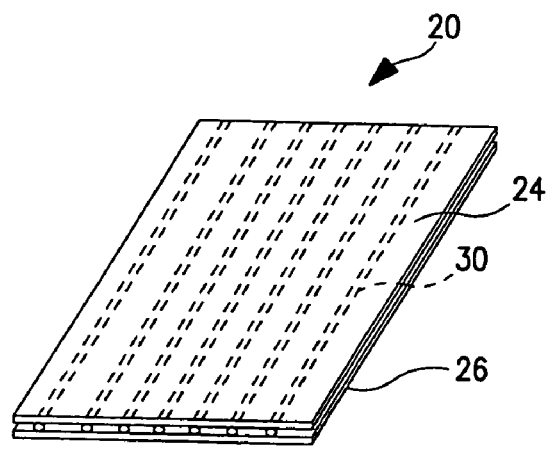
FIG. 4 is a perspective view of yet another embodiment of an elastomeric substrate used to make an absorbent, elastomeric material.
Figure 5:
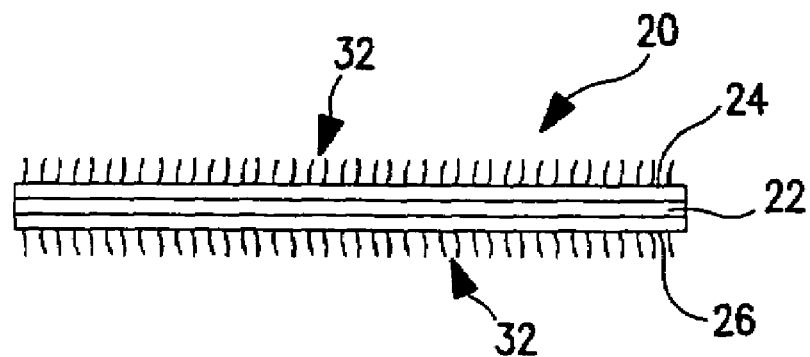
FIG. 5 is a cross-sectional view, taken along line 5-5 of FIG. 2 of one embodiment of an elastomeric substrate used to make the absorbent, elastomeric material.
Figure 5B:
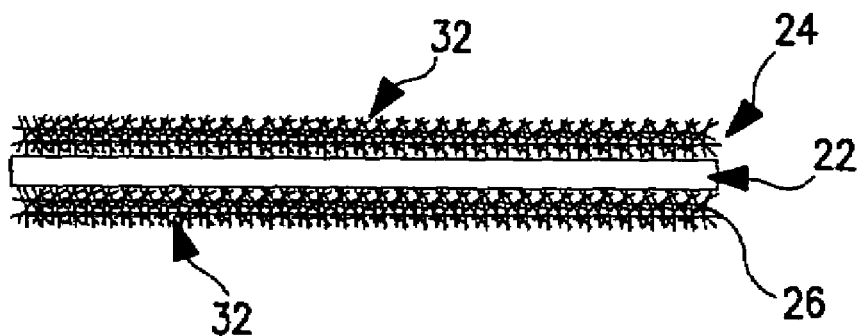
FIG. 5b is another cross-sectional view, taken along line 5-5 of FIG. 2, of another embodiment of an elastomeric substrate used to make the absorbent elastomeric material of the invention.

FIG. 2 illustrates an elastomeric substrate 20 including an elastic film 22 laminated between two nonwoven facings 24, 26. FIG. 3 illustrates an elastomeric substrate 20 including an elastic foam 28 laminated between two nonwoven facings 24, 26. FIG. 4 illustrates an elastomeric substrate 20 including a number of elastic strands 30 laminated between two nonwoven facings 24, 26. FIG. 5 is a cross-sectional view of FIG. 2, taken along line 5-5, showing fibers 32 extending from the nonwoven web facings 24, 26. FIG. 5b is another cross-sectional view of FIG. 2, taken along line 5-5, showing rugosities of high-loft bonded carded web facings 24, 26 along with the fibers 32 which protrude from the irregular plane of the rugose high-loft carded web.

Figure 5C:
FIGS. 5c and 5d illustrate a stiffened elastic material.
Figure 5D:
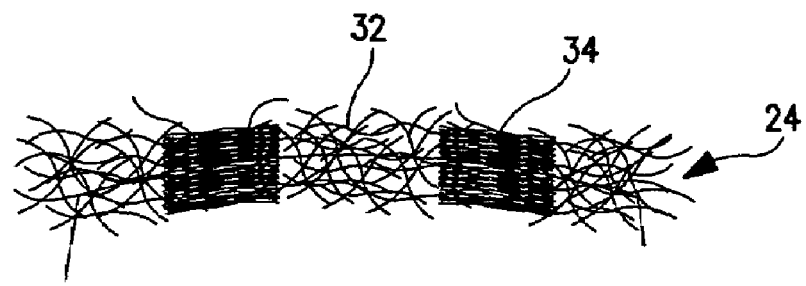
Figure 5E:
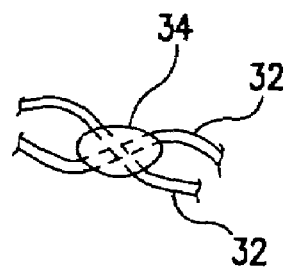
FIG. 5e illustrate fibers of the stiffened elastic material.
Figure 6:
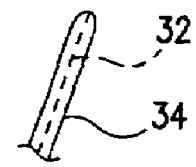
FIG. 6 illustrates a fiber of the absorbent, elastomeric material.

The attached material can include a superabsorbent polymer. FIG. 6 illustrates a single fiber 32, representative of many fibers, of the elastomeric substrate 20 with a superabsorbent polymer 34 non-adhesively applied and/or attached to, or encasing, the fiber 32. FIGS. 5c, 5d and 5e illustrate alternative types of structures. In FIG. 5c the superabsorbent 34 only partially encases the fibers 32, while in FIGS. 5d and 5e the superabsorbent 34 encases many fibers 32. The resulting superabsorbent is not in the form of particles trapped by surrounding fibers but instead is in the form of particles that encase or bond firmly to fibers because the particles were polymerized or crosslinked while in contact with or even surrounding the fibers, as shown in FIG. 5e. Therefore, the superabsorbent material in this invention is not held onto the web by any type of adhesive or glue.

The superabsorbent polymer 34 can include, for example, alkali metal salts of polyacrylic acids; polyacrylamides; polyvinyl alcohol; ethylene maleic anhydride copolymers; polyvinyl ethers; hydroxypropylcellulose; polyvinyl morpholinone; polymers and copolymers of vinyl sulfonic acid, polyacrylates, polyacrylamides, polyvinyl pyridine; and the like. Other suitable polymers include hydrolyzed acrylonitrile rafted starch, acrylic acid grafted starch, and isobutylene maleic anhydride copolymers and mixtures thereof. Further suitable polymers include inorganic polymers such as polyphosphazene and the like.

Typically, a superabsorbent material is capable of absorbing at least about 15 times its weight in 0.9 weight percent sodium chloride, and desirably is capable of absorbing more than about 30 times its weight in 0.9 weight percent sodium chloride. Suitable superabsorbent materials are available by, for example, following the teachings in U.S. Pat. 4,500,315 issued 19 Feb. 1985 to Pieniak et al., incorporated herein by reference, using ISOBAM 18 available from the Kuraray America, Inc. of New York, N.Y., and diethylene triamine cross-linker, the emulsion method of PCT Publication No. WO 00/50096 published 31 Aug. 2000 by Gartner et al., incorporated herein by reference, or using a suitable mixture of monomer, cross-linker, initiators and small superabsorbent particles per the teachings in U.S. Pat. No. 6,417,425 issued 09 Jul. 2002 (previously published as PCT Publication No. WO 01/56625) to Whitmore et al., incorporated herein by reference, or the method of U.S. Pat. No. 5,962,068, issued 05 Oct. 1999 to Tsuchiya et al., herein incorporated by reference, wherein the redox initiated polymerizing superabsorbent is applied to the web early enough to surround fibers, not just to have a few particles apply and!or attach to the fibers, thereby leaving the rest of the particles to apply and/or attach to other particles.

The superabsorbent polymer 34 is applied and/or attached to the elastomeric substrate 20 by surrounding fibers 32 in the substrate or by bonding the superabsorbent to itself or fibers in the nonwoven web with, for example, crosslinkers in a superabsorbent polymer or prepolymer solution. Crosslinking may, for example, be bonds which range from highly ionic to highly covalent types of bonds or the like. These bonds can further be augmented with hydrogen bonds and/or induced polar bonds. The superabsorbent polymer can be in a solution at a concentration of between about 5% and about 30% by weight, or between about 10% and about 25% by weight, or between about 15% and about 22% by weight. Superabsorbent prepolymer solutions can be in concentrations of appropriate monomers, initiators and crosslinkers and the like of between about 25% and 75% by weight, or between about 30% and about 60% by weight, or between about 40% and 55% by weight.

Other methods of applying and/or attaching the superabsorbent polymer 34 to the elastomeric substrate 20 include saturation, printing, coating, and spraying. Examples of suitable application methods are taught in U.S Pat. No. 4,500,315 issued Feb. 19, 1985, PCT Publication No. WO 00/50096 published Aug. 31, 2000, European Patent Application No. 0 947 549 A1 published Oct. 6, 1999, PCT Publication No. WO 01/56625 A2 (now U.S. Pat. No. 6,417,425), and in U.S. Pat. No. 5,962,068 issued Oct. 5, 1999 to Tsuchiya et al., all of which are herein incorporated by reference. In one particular method, namely an in-situ polymerization superabsorbent coating process, a superabsorbent monomer solution consisting of monomer, crosslinkers and initiators is sprayed onto the substrate, the sprayed substrate is exposed to UV radiation and/or other radiation in order to polymerize and crosslink the monomer, and the irradiated substrate is then exposed to heat to remove any remaining moisture. In another method, the nonwoven web is coated on one or both sides with superabsorbent polymer containing activatable cross-linkers which are activated to cross-link the superabsorbent polymer. These methods result in 25 to 95 percent superabsorbent polymer in the web.

Other elastic materials may be used as the elastomeric material of the stiffened elastic material. Examples of elastic materials include a vertical filament laminate made up of 17 gsm bonded carded web laminated to stretched KRATON® filaments with a resultant basis weight of about 150 gsm, or the previously mentioned elastomeric high-loft bonded carded web. Still others include incorporation of an elastic film, or elastic foam laminated between two nonwoven web facings or even an elastic foam by itself. The substrate may be elastic in either one direction or in more than one direction. The substrate may be either liquid-permeable or liquid-impermeable regardless of whether the substrate is in a stretched or unstretched state.

Besides superabsorbent polymers, other examples of attached materials include decorations or other desirable materials such as strengthening agents (e.g., superabsorbent surface crosslinkers, and wet strength resins) medicinal delivery agents, and the like. As used herein, "decorations" mean anything that improves the aesthetics or attractiveness of the elastomeric structure.

According to the present invention, elasticity can be restored to a stiffened elastic material by stretching in the machine direction (MD) and/or cross-machine direction (CD) and/or another direction, compressing, and/or notching the stiffened elastomeric material. These methods can be used alone or in combination for a compounding effect.

Figure 7:
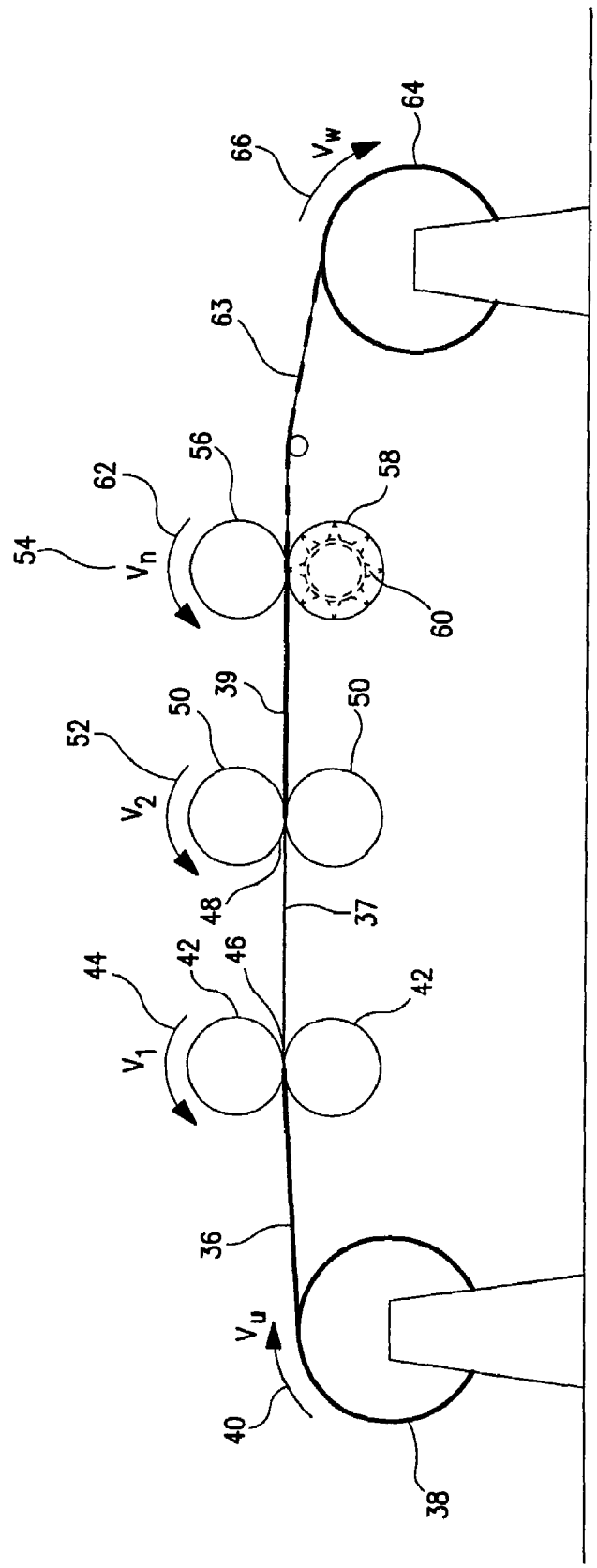
FIG. 7 is a schematic of an apparatus and method for prestretching, compressing, and notching a stiffened elastic material all in one operation.

FIG. 7 illustrates an apparatus and method of restoring elasticity to a stiffened elastic material primarily in the MD including the steps of prestretching, compressing and notching the stiffened elastic material all in one operation. Not shown are methods for prestretching in the CD by for example use of Mount Hope rolls, machine direction intermeshing grooved rolls, and tentering methods as well as notching methods parallel to the MD and the like. Referring to FIG. 7, the stiffened elastic material 36 is provided from an unwind stand 38. Alternatively, the stiffened elastic material 36 may be provided directly from a production unit in a continuous process (not shown). Any of the previously described stiffened elastic materials can be suitable for the stiffened elastic material 36. The unwind stand 38 unwinds the stiffened elastic material 36 at a speed $V_u$ in the direction shown by arrow 40 towards a first set of calender rollers 42. The calender rollers 42 rotate in the direction shown by arrow 44 at a speed $V_1$ which should be greater than or equal to $V_u$. The stiffened elastic material 36 proceeds between the calender rollers 42 to nip 46. The stiffened elastic material 36 is prestretched in the section between nip 46 and nip 48, as illustrated by the thinner line in this section. The stiffened material 36 continues toward nip 48 which is formed by a second set of calender rollers 50 which rotate in the direction shown by arrow 52 at a speed $V_2$ which should be greater than $V_1$. In order to prestretch the stiffened elastic material 36 to 150% of its original unstretched length, $V_2$ should be about 2.5 times $V_u$. $V_2$ and/or $V_u$ can be adjusted in order to obtain a different desired percentage stretch. After the now prestretched material 37 passes through the calender rollers 50, it is allowed to contract as illustrated by the thicker line after the calender rollers 50. As an alternative to this format, if the unwind stand 38 is driven at a controlled surface speed, the first set of calender rollers 42 could be eliminated so that the prestretching would occur between the unwind stand 38 and the nip 48 formed by the second set of calender rollers 50. Any other stretching method known to one skilled in the art may also be used in order to accomplish the prestretching step.

As previously mentioned, the stiffened elastic material must be prestretched beyond which the finished material will be stretched in use, that is, beyond the "usable stretch" of the finished elastic material. The "usable stretch" depends on the end use of the finished elastic material. For example, if the finished elastic material will be used in, or integrated into certain types of personal care absorbent products, then the "usable stretch amount" would be about 80% and the stiffened elastic material should be prestretched beyond about 100% or prestretched beyond about 125% or prestretched beyond about 150%. Alternatively, if the finished elastic material will be used in, or integrated into certain types of sweat bands, then the "usuable stretch amount" would be about 30%, and the stiffened elastic material should be prestretched beyond about 40% or prestretched beyond about 50% or prestretched beyond about 60%. In general, to obtain a desired "usable stretch amount" the stiffened elastic material should be prestretched at least about 25% more than the desired "usable stretch amount," or at least about 50% more than the desired "usable stretch amount," or at least about 75% more than the desired "usable stretch amount."

The compressing step can occur either between the first set of calendar rolls 42 or between the second set of calender rollers 50. The compressing can occur with a fixed gap between the calender rollers 42 and/or 50. The fixed gap can be a distance between the calender rollers 42 and/or 50 in a range of about 0.005 inches to about 0.05 inches or in a range of about 0.006 inches to about 0.04 inches or in a range of about 0.007 inches to about 0.03 inches. The gap distance can be adjusted depending on the desired thickness for the resulting material, the initial thickness of the material, or the desired amount of compression. Pneumatic air cylinders (not shown) can be used to push bearing pillow blocks supporting the calender rollers 42 and/or 50 against stops such that a resultant force of greater than about 500 pounds per lineal inch (pli) of web width or greater than about 750 pli of web width or greater than about 1000 pli of web width is applied to the web in order to insure the stiffened elastic material is adequately compressed. In the alternative, the compressing can occur without a fixed gap between calender rollers 42 and/or 50, but with varying pneumatic air cylinder pressure to create a resultant force of greater than about 200 pounds per lineal inch (pli) of web width or greater than about 500 pli of web width or greater than about 750 pli of web width is applied to the web. The pneumatic air cylinder pressure can be varied depending on the desired thickness for the resulting material or the desired amount of compression. Any other compressing method known to one skilled in the art may also be used in order to accomplish the compressing step.

The calender rollers 42 and 50 can have embossing patterns or can be smooth. Alternatively, the calender rollers 42 and 50 can have a rough surface to prevent slippage of the material passing through them.

After the now prestretched and compressed material 39 passes through the calender rollers 50, it proceeds toward the notching device 54. The notching device 54 includes an anvil roller 56 and a die cutting roll 58. The die cutting roll 58 includes raised sharp areas or protrusions 60 that cut the material in discreet desired locations. The die cutting roll 58 is positioned so that the protrusions 60 do not contact the anvil roll 56. The protrusions 60 can be any desired shape to correspond to the desired shape for the notches in the material. The anvil roll 56 rotates at a speed $V_n$ in the direction of arrow 62. $V_n$ should be less than or equal to $V_2$. Any other notching method known to one skilled in the art may also be used in order to accomplish the notching step.

The prestretched, compressed and notched finished material 63 then proceeds from the notching device 54 towards a wind-up stand 64 which rotates in the direction of arrow 66 at a speed $V_W$. $V_W$ should be less than or equal to $V_n$. In addition, $V_W$ should be greater than or equal to $V_u$. Alternatively, the prestretched, compressed and notched material 63 may be provided directly to a converting operation in a continuous process (not shown).

As previously described with respect to FIG. 7, the prestretching, compressing and notching methods can be used in combination for a compounding effect depending on the amount of elasticity to be restored. Alternatively, any one of these methods can be used alone. Alternatively, any one of these methods can be used with any one of the other methods. For example, if notching is not desired, the notching device 54 can be eliminated so that the material proceeds directly from the second set of calender rollers 50 to the wind-up stand 64 so that only the stretching and compressing steps are used. Alternatively, if compressing is not desired, the second set of calender rollers 50 can be eliminated so that the material proceeds directly from the first set of calender rollers 42 to the notching device 54 so that only the stretching and notching steps are used. Alternatively, if prestretching is not desired, the first set of calender rollers 42 can be eliminated so that the material proceeds directly from the unwind stand 38 to the calender rollers 50. In addition, these methods may be carried out in different orders. For example, and as described in Example 2 below, the compressing step may occur prior to the prestretching step.

Figure 8:
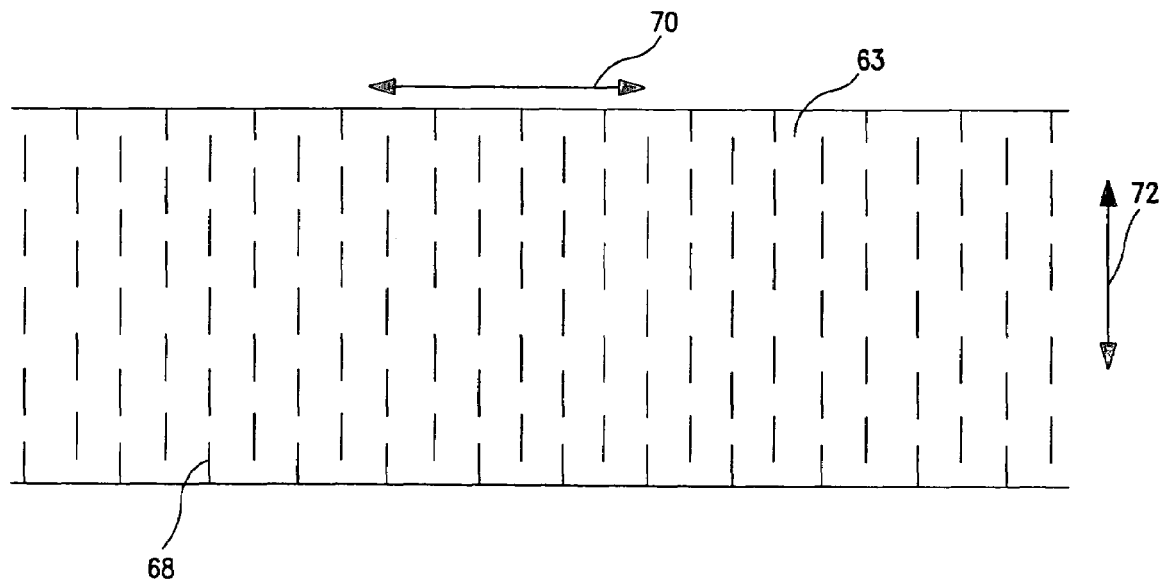
FIG. 8 illustrates a notching pattern in an elastic material according to the present invention.
Figure 9:
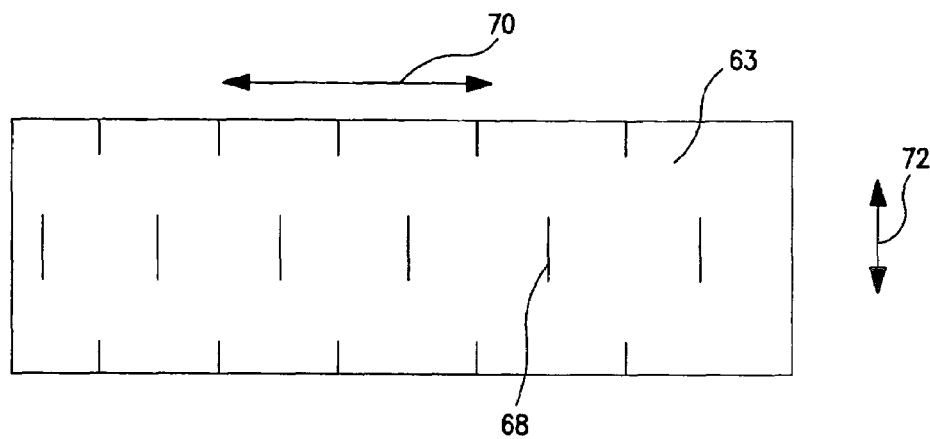
FIG. 9 illustrates an alternative notching pattern in an elastic material according to the present invention.

When the finished material 63 is notched, there are a variety of possible notch patterns. Referring to FIG. 8, finished material 63 includes notches 68. The notches 68 can overlap such that any straight elastomeric elements in the machine direction (MD) illustrated by arrow 70 cannot extend beyond every other notch 68 in the machine direction. Alternatively the notches can be arranged to overlap in the cross-machine and/or some can be aligned in the MD and others can be aligned in the CD. As shown notches 68 can be about 0.25 cm to about 3 cm in length in the cross-machine direction illustrated by arrow 72 and spaced about 0.25 cm to about 5 cm apart in the cross-machine direction. In addition, notches can be about 0.25 cm to about 5 cm apart in the machine direction. Notches 68 which are not on the same cross-machine direction line can overlap as shown in FIG. 8 up to about 40% of the length of the notch 68. Alternatively, as shown in FIG. 9, notches 68 which are not on the same cross-machine direction line can be spaced apart up to about 5 cm so as not to overlap. Additional and more complicated patterns are possible and contemplated including putting notches at an angle to the machine direction. Notches 68 can be any desired shape, such as straight lines, curved lines, diagonal lines, crosses, stars or the like.

STIRBAR RETENTION TEST

This test is a measure of superabsorbent attachment to a web when the superabsorbent has been fully swollen. This test was designed to simulate the worst conditions that a superabsorbent nonwoven composite would encounter inside of a swim pant.

The procedure for carrying out the stirbar retention test is as follows:
1. From the material being tested cut out a 3 centimeter (cm) by 3 cm sample of known or determined substrate basis weight or of known initial SAP concentration.
2. Place the sample in an oven at 105 degrees Celsius for one hour to obtain an initial dry weight.
3. Measure and record the sample initial weight.
4. Soak the sample in an excess of 0.9 weight percent saline for 30 minutes.
5. Place the sample in a 250 ml beaker filled with 200 ml of tap water.
6. Stir at 400 rpm using a 9 millimeter (mm) by 37 mm magnetic, TEFLON®-coated stirbar for 5 minutes.
7. Place the sample in oven overnight (16 hours) at 80 degrees Celsius.
8. Measure and record the sample final dry weight.
9. Calculate the percent retention using the following expression:

$$\% \text{ SAP retained} = 100 \times \left(1 - \frac{\text{initial weight} - \text{final weight}}{\text{initial weight} \times \text{initial SAP concentration}}\right)$$

where "initial SAP concentration," if known, must be corrected to be on a 1 hour 105 degree Celsius dry basis or if the substrate basis weight is known or can be determined is equal to:

1−(substrate basis weight in gsm×0.0009/ initial weight).

EXAMPLES

Example 1

An elastomeric high-loft bonded carded web was spray coated with a superabsorbent monomer solution, the web was exposed to radiation energy to initiate polymerization and the excess moisture was dried following the teachings of U.S. Pat. No. 6,417,425 issued 9, Jul. 2002 to Whitmore et al., herein incorporated by reference. The nonwoven substrate was a vertical filament laminate made up of 17 gsm bonded carded web laminated to stretched KRATON® filaments with a resultant basis weight of about 150 gsm. The superabsorbent add-on was about 125 gsm.

Figure 10:
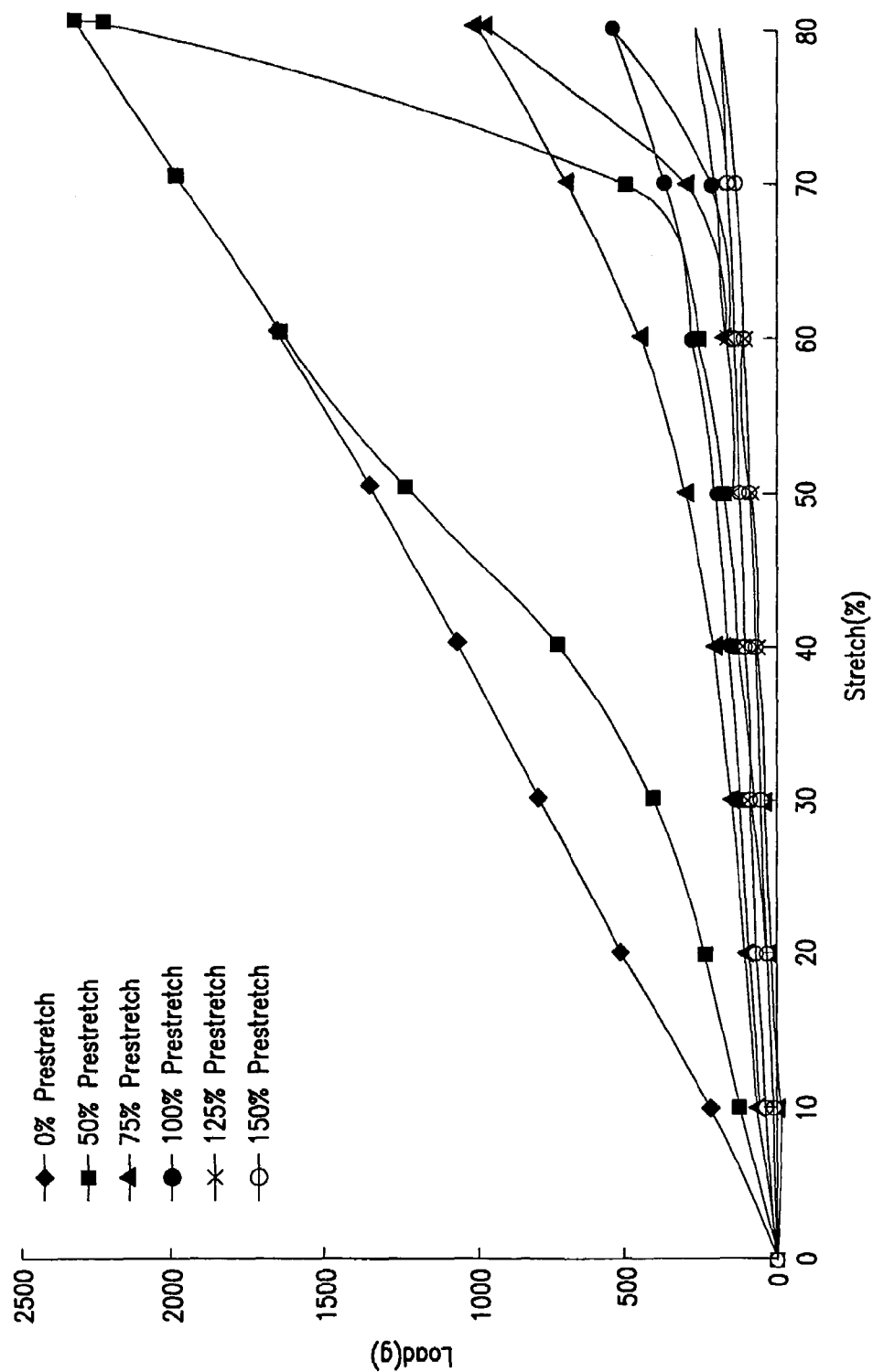
FIG. 10 illustrates load vs. elongation extension and retraction curves showing the effect of prestretching on the elastic modulus of an elastomeric nonwoven web.

FIG. 10 illustrates load vs. elongation extension and retraction curves which demonstrate the reduction in load needed to stretch the stiffened elastic material after it has been prestretched (i.e., stretched before actual use) to 150% of its original length. Before being prestretched, the load needed to stretch a 2-inch piece of material 80% was about 2300 grams/2 inches. After being stretched 100% and 150%, the load needed to stretch the material 80% of its new length dropped to 500 grams/2 inches and 160 grams/2 inches, respectively, and the hysteresis loss was significantly smaller, which implies that most of the bonds between fibers caused by the attached superabsorbent had been broken. An important side observation from this data is that prestretching at distances less than the distance to which the material will eventually be stretched does not have an adequate effect on restoring elasticity. Another observation is that the attached material should be in its stiffened state (e.g., the superabsorbent should be dry) so that the attached material does not just deform instead of bonds actually being broken when prestretched.

Comparing load vs. elongation extension and retraction curves for FIG. 10 and FIG. 1, it is seen that prestretching the stiffened elastic material to 150% of its original length restores the elastic properties that the elastic material exhibited prior to the attachment of the superabsorbent polymer. That is, the data for the 150% prestretch sample for FIG. 10 is about equivalent to the data for the sample untreated with superabsorbent polymer in FIG. 1

Example 2

Figure 11:
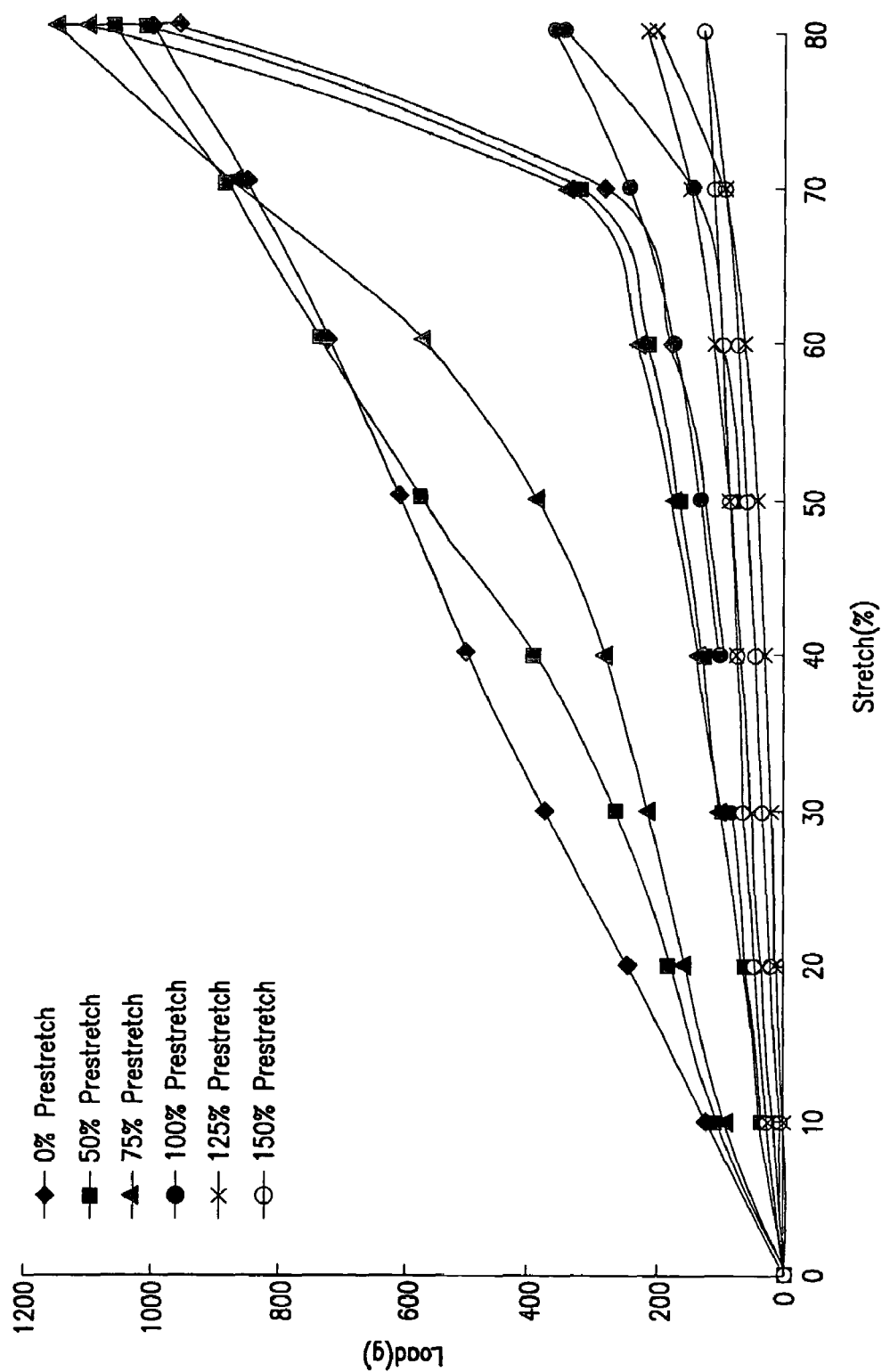
FIG. 11 illustrates load vs. elongation extension and retraction curves showing the effect of compressing then prestretching an elastomeric nonwoven web.

Experimental data was collected using the nonwoven previously discussed in Example 1. Samples were compressed prior to prestretching in the nip with the nip setting of 0.007 inch gap and a force of about 700 pli due to air pressure applied to the pneumatic air cylinders. FIG. 11 illustrates load vs. elongation extension and retraction curves which demonstrate the combined effects of prestretching and compressing the nonwoven. The 0% prestretch curve shows the effect of compression only. Notice that FIG. 10 shows the unmanipulated sample (i.e., the 0% prestretched sample) at a load to stretch 80% of 2300 grams/2 inches as compared to 1000 grams/2 inches required for the compressed sample shown in FIG. 11. Prestretching appears to have a more significant effect but when used in combination with compression the effect is further improved. Also the material is smoother/less rough with compression.

Example 3

Experimental data from the previously mentioned nonwoven from Example 1 showed that the load needed to stretch 80% was reduced from 1875 grams/2 inches to 800 grams/2 inches by the notches cut in the web. When notches were used in combination with compression, the load was further reduced to 700 grams/2 inches.

Example 4

Using the elastomeric high-loft bonded carded web of Example 1, except with a basis weight of about 134 gsm, about 65 gsm of superabsorbent polymer was applied using the process of Example 1. This sample was compressed in a nip with a 0.007 inch gap and prestretched about 150% after insuring the moisture content was less than about 10%. The Stirbar Retention Test was run on this sample and one that was not nipped and prestretched. The superabsorbent retention on the finished elastic material was only reduced to 48% with nipping and prestretching versus 58% superabsorbent retention without nipping and prestretching for a reduction of about 17%.

Reduction in superabsorbent polymer Stirbar Retention due to methods of restoring elasticity are desirably less than about 30% or less than about 20% or less than about 10%. Actual superabsorbent polymer Stirbar Retention is desirably greater than about 40% or greater than about 60% or greater than about 80%.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A method of preparing an elastic absorbent composite, comprising:
    providing a fibrous elastic substrate having a usable stretch amount of at least 80% in at least one direction;
    applying a superabsorbent prepolymer solution to the fibrous elastic substrate; crosslinking the superabsorbent prepolymer on the substrate to provide superabsorbent polymer particles that encase or firmly bond the fibers of the substrate, thereby forming a stiffened absorbent composite; and
    stretching the stiffened absorbent composite by an amount at least 25% greater than the usable stretch amount of the fibrous elastic substrate in said at least one direction to provide the elastic absorbent composite.

2. The method of claim 1, comprising stretching the stiffened absorbent composite by an amount at least 50% greater than the usable stretch amount.

3. The method of claim 1, comprising stretching the stiffened absorbent composite by an amount at least 75% greater than the usable stretch amount.

4. The method of claim 1, comprising stretching the stiffened absorbent composite to at least 150% of its original length.

5. The method of claim 1, comprising stretching the stiffened absorbent composite in more than one direction.

6. The method of claim 1, wherein the stiffened absorbent composite further comprises a decoration.

7. The method of claim 1, wherein the stiffened absorbent composite further comprises a strengthening agent.

8. The method of claim 7, wherein the strengthening agent comprises a wet strength resin.

9. The method of claim 1, further comprising compressing the stiffened absorbent composite.

10. The method of claim 1, further comprising notching the stiffened absorbent composite.

11. The method of claim 9, further comprising notching the stiffened absorbent composite.

12. A method of preparing an elastic absorbent composite, comprising:
    providing a fibrous elastic substrate;
    applying a superabsorbent prepolymer solution to the fibrous elastic substrate;
    crosslinking the superabsorbent prepolymer on the substrate to provide superabsorbent polymer particles that encase or firmly bond the fibers of the substrate, thereby forming a stiffened absorbent composite; and
    compressing the stiffened absorbent composite to provide the elastic absorbent composite.

13. The method of claim 12, comprising compressing the stiffened absorbent composite between calender rollers having a fixed gap.

14. The method of claim 13, wherein the fixed gap comprises a distance between the calender rollers in a range of about 0.005 inches to about 0.05 inches.

15. The method of claim 13, wherein the fixed gap comprises a distance between the calendar rollers in a range of about 0.006 inches to about 0.04 inches.

16. The method of claim 13, wherein the fixed gap comprises a distance between the calender rollers in a range of about 0.007 inches to about 0.03 inches.

17. The method of claim 12, wherein a force on the stiffened elastic material is greater than about 200 ph.

18. The method of claim 17, wherein the force on the stiffened elastic material is greater than about 500 ph.

19. The method of claim 17, wherein the force on the stiffened elastic material is greater than about 750 ph.

20. The method of claim 12, further comprising stretching the stiffened absorbent composite.

21. The method of claim 12, further comprising notching the stiffened absorbent composite.

22. The method of claim 20, further comprising notching the stiffened absorbent composite.

23. A method of preparing an elastic absorbent composite, comprising:
    providing a fibrous elastic substrate;
    applying a superabsorbent prepolymer solution to the fibrous elastic substrate;
    crosslinking the superabsorbent prepolymer on the substrate to provide superabsorbent polymer particles that encase or firmly bond the fibers of the substrate, thereby forming a stiffened absorbent composite; and
    passing the stiffened absorbent composite through a notching device to notch the stiffened absorbent composite, thereby providing the elastic absorbent composite.

24. The method of claim 23, wherein the notching device comprises an anvil roller and a die cutting roller.

25. The method of claim 23, wherein the notching device comprises protrusions.

26. The method of claim 23, further comprising stretching the stiffened absorbent composite.

27. The method of claim 23, further comprising compressing the stiffened absorbent composite.

28. The method of claim 26, further comprising compressing the stiffened absorbent composite.

29. The method of claim 23, wherein a finished material comprises notches which overlap.

30. The method of claim 23, wherein notches in a finished material are about 0.25 cm to about 3 cm in length.

31. The method of claim 23, wherein notches in a finished material are spaced about 0.25 cm to about 5 cm apart.

32. An elastic absorbent composite, comprising:
    a fibrous elastic substrate having a usable stretch amount of at least 80% in at least one direction;
    a superabsorbent polymer non-adhesively attached to the fibrous elastic substrate in a manner that forms a stiffened absorbent composite;
    wherein elasticity has been restored to the absorbent composite by treating the stiffened absorbent composite in a manner selected from the group consisting of stretching the stiffened absorbent composite by an amount at least 25% greater than the usable stretch amount of the fibrous elastic substrate in the at least one direction, compressing the stiffened absorbent composite, notching the stiffened absorbent composite, and combinations thereof.

33. The elastic absorbent composite of claim 32, wherein the stiffened absorbent composite further comprises a decoration.

34. The elastic absorbent composite of claim 32, wherein the stiffened absorbent composite further comprises a strengthening agent.

35. The elastic absorbent composite of claim 32, wherein the elastic absorbent composite has a superabsorbent retention of greater than about 40%.

36. The elastic absorbent composite of claim 32, wherein the elastic absorbent composite has a superabsorbent retention of greater than about 60%.

37. The elastic absorbent composite of claim 32, wherein the elastic absorbent composite has a superabsorbent retention of greater than about 80%.

38. The elastic absorbent composite of claim 32, wherein the elastic absorbent composite includes overlapping notches.

39. The elastic absorbent composite of claim 38, wherein the notches overlap in a machine direction.

40. The elastic absorbent composite of claim 32, wherein the elastic absorbent composite includes notches having a length between about 0.25 cm and about 3 cm.

41. The elastic absorbent composite of claim 32, wherein the elastic absorbent composite includes notches that are spaced apart from about 0.25 cm to about 5 cm.

* * * * *